United States Patent [19]

Porzsolt et al.

[11] 4,081,241

[45] Mar. 28, 1978

[54] DIAGNOSTIC PROCESS

[75] Inventors: Franz Porzsolt, Hachborn; Christoph Tautz, Tubingen; Rudolf Schmidtberger, Marburg an der Lahn; Wolfgang Ax, Wehrda; Burkhard Enders, Marburg an der Lahn, all of Germany

[73] Assignee: Behringwerke Aktiengesellschaft, Marburg an der Lahn, Germany

[21] Appl. No.: 608,704

[22] Filed: Aug. 28, 1975

[30] Foreign Application Priority Data

Aug. 30, 1974 Germany .................... 2441536

[51] Int. Cl.² .................... G01N 27/26; G01N 33/16
[52] U.S. Cl. .................... 23/230 B; 204/180 R; 424/12
[58] Field of Search .................... 23/230 B; 204/180 R; 424/12; 356/105

[56] References Cited

U.S. PATENT DOCUMENTS

| | | | |
|---|---|---|---|
| 3,826,613 | 7/1974 | Parikh et al. | 23/230 B |
| 3,914,400 | 10/1975 | Shulman et al. | 424/12 |
| 3,984,533 | 10/1976 | Uzgiris | 23/230 B X |
| 3,988,115 | 10/1976 | Modabber | 23/230 B |
| 3,999,944 | 12/1976 | Grosser | 23/230 B |

OTHER PUBLICATIONS

*Science*, v. 153, pp. 80–82 (1966).
*Notore*, v. 218, pp. 1078–1079 (1968).
*Chem. Abstr.*, v. 74:30377y (1971).
*Chem. Abstr.*, v. 57:17266b (1962).
*Chem. Abstr.*, v. 65:9516q (1966).

*Primary Examiner*—Sidney Marantz
*Attorney, Agent, or Firm*—Curtis, Morris & Safford

[57] ABSTRACT

An in vitro method for the diagnosis of immunization states which involves measuring, in an electric field, the changed mobility of charged indicator particles, other than macrophages, which particles have been treated with (1) a suspension of lymphocytes that have been incubated with an antigen or (2) the cell-free supernatant of such a suspension of incubated lymphocytes.

4 Claims, No Drawings

DIAGNOSTIC PROCESS

The present invention relates to a process for the in vitro diagnosis of the state of immunization present in the cells of human beings and animals, which process comprises measuring, in an electric field, the changed mobility of charged indicator particles which have been treated with a suspension of lymphocytes which have been incubated with an antigen, or treated with the cell-free supernatant of such a suspension.

It is known that lymphocytes of persons suffering from various diseases can be stimulated by antigens so as to release substances which change the migration speed of guinea pigs macrophages in an electric field. This principle was reported by Field and Caspary for the diagnosis of tumors. In the meantime, possibilities have been recognized for using this method for the detection and differential diagnosis of a number of further diseases, for example bronchial asthma, multiple sclerosis, scrapie, neurological diseases and thyroidal diseases, furthermore for the control of the thymus function. In transplantation immunology, the method can be used for donor-donee selection and observation of the post-transplantation situation. The modified migration speed of the macrophages can be measured in commercial-type cell electrophoresis apparatus (cytopherometers) and evaluated for the clinical diagnosis.

The method of Field and Caspary or of Pritchard et al. is based especially on the prejudicial idea that macrophages necessarily have to be used. These, however, can only be obtained from healthy test animals, such as guinea pigs, by an expensive technique and can be used for only a short time. In the preparation of the macrophages from guinea pigs, a number of various cell populations are obtained which migrate at a different speed in an electric field; therefore, a specific population has to be selected for measuring purposes, which is another problem of this method. Macrophages taken from diseased animals cannot be used in the test system of Field and Caspary.

Hence, there was a demand for replacing the macrophages by charged indicator particles of a fairly homogeneous size and shape which, owing to their stability, can be used for a prolonged period of time and, owing to the homogeneity of the electric charge and of their appearance, allow a simple evaluation of the measurement in the electrophoretic migration.

It has been found that the diagnostic process can be adequately carried out using, instead of macrophages, particles which show a substantially uniform behavior in an electric field, which enter into linkages with or, in the broadest sense of the word, undergo interactions with suitable test substances, such as a lymphocytic medium, so that the behavior of the particles in the electric field is altered in a measurable manner and the particles can directly be observed or measured by means of adequate equipment. Human or animal erythrocytes that have been treated with denaturing agents, for example with tannin and/or sulfosalicyclic acid, are to be used especially as indicator particles. The macrophages can also be replaced by charged particles of a plastic material, for example by latex particles.

Hence, an object of this invention is a diagnostic in-vitro process wherein lymphocytes are incubated with antigens, the incubation mixture or the cell-free supernatant thereof is added to a dispersion of indicator particles, and the migration speed of the indicator particles in an electric field is measured, the indicator particles used being particles which show a substantially uniform behavior in the electric field and undergo interactions with the lymphocyte supernatant, thus modifying the behavior of the particles in the electric field in a measurable manner.

The chemical nature of the factors contained in the supernatant, which factors are able to undergo interactions with the indicator particles, has not yet been elucidated. The substances under discussion are, for example, the lymphocyte products "macrophage slowing factor" (MSF) and "migration inhibition factor" (MIF). The antigens used are generally antigens soluble in an aqueous medium but also particular antigens, such as cells or shaped cell constituents. Soluble antigens are, for example antigens of microorganisms and of higher animals, vegetable lectins and other antigens of natural or synthetic origin.

When an antigen which is specific for the diagnosis of a certain immunity is used, the lymphocytes of a test person, who is sensitized to this antigen, are stimulated. The substances released in the ambient solution change the excess charge of the indicator particles in comparison to the indicator particles obtained with the media from incubations, with the same antigen of lymphocytes of persons who show no reaction. As specific antigens for the diagnosis antigens, such as tuberculin, tetanus toxoid and streptococcal antigens have been accepted, as standards for the immunization caused in the cells. Further antigens of lesser specificity are known to indicate the presence of general-type diseases in the body when identified. There is, for example, a relation between the encephalitogenic factor (EF) and cancer.

According to the process of the invention, lymphocytes of test persons are obtained from blood or lymph or from tissues of lymphoidal organs. When blood is used, this is made non-coagulating, for example by adding heparin. The lymphocytes are recovered by one of the known methods, for example by filling the blood sample into a column charged with glass beads, to which adherent cells stick. The lymphocytes can then be isolated from the eluate by gradient-centrifuging and the incubated for 60 minutes to 24 hours at 20°-37° C with the diagnostic antigen in an antigen/lymphocyte ratio which is constant during the test. The incubation mixture of the angtigen with the lymphocytes or the incubation supernatant separated from the lymphocytes is used to charge the indicator particles used instead of the macrophages. For this purpose, the indicator particles, preferably tanned erythrocytes, especially those which are additionally stabilized with sulfosalicylic acid according to the process of Becht (J. Immunol. 101, p. 18-22 (1968)) are incubated in a suspension of $1 \times 10^7$ to $5 \times 10^7$ per ml with the incubation mixture or the supernatant thereof for 30 to 120 minutes at 20°-40° C.

The ratio of antigen to lymphocytes is determined in a preliminary test by adding an increasing amount of antigen to a constant number of about $0.5 \times 10^6$ to $1 \times 10^6$ lymphocytes per ml of medium, and then recording the optimum influence on the migration speed of the indicator particles.

As latex particles to be used according to the invention as indicator particles, those contained in latices of high molecular weight compounds of natural or synthetic origin are generally suitable, provided they possess the aforementioned electrophoritic properties. The size of the particles should correspond approximately to the size of denatured erythrocytes, i.e. to about $5 \times 10^{-4}$ 9 $\times 10^{-4}$ cm. The concentration of the particles in the liquid, preferably aqueous phase of the latex advantageously ranges from $1 \times 10^7$/ml to $5 \times 10^7$/ml in case electrophoresis is carried out in a cytopherometer manufactured by Messrs. Carl Zeiss, W. Germany. If different electrophoresis equipment is used, the particle concentration should be adjusted to the values optimum for each individual apparatus. In some cases, these values differ from the said concentration value by some decimal powers. Suitable latex materials are, especially, latices of plastic materials, and among these, preferably latices of polystyrene or copolymers of styrene with suitable comonomers, for example divinyl-benzene. The chemical nature of the latex particles is, however, not critical for the process of the invention.

The so-obtained suspension of the treated indicator particles is then fed into a cell electrophoresis system which allows recording of the migration speed. Evaluation is made by determining the deviation of the electrophoretic migration speed from the zero value and from the value of unreacting control persons. When, for example, an encephalitogenic factor(EF) as the antigen is incubated with lymphocytes of a person supposed to suffer from a tumor, and when the incubation medium causes the electrophoretic mobility of the erythrocytes treated therewith to slow down as compared with erythrocytes that have been incubated only with a physiologically acceptable incubation medium (zero value) and as compared with erythrocytes that have been incubated with an incubation medium obtained from lymphocytes of healthy persons used as control, which lymphocytes do not react upon incubation with EF (normal value), a pathological evaluation of the diagnosis is made.

When, for example, tetanus toxoid or purified tuberculin as the antigen is incubated with lymphocytes and the incubation medium causes the electrophoretic mobility of the erythrocytes charged therewith to slow down as compared to erythrocytes that have been incubated with the supernatant of an antigen-free lymphocyte culture, the donor of the erythrocytes is found to be sensitized against the antigen used. The positive result is moreover taken as a standard for the cellular immunization situation of the donor of the lymphocytes.

When, instead of a soluble antigen, $0.5 \times 10^6$ to $2 \times 10^6$ lymphocytes of a second donor are incubated with $0.5 \times 10^6$ to $2 \times 10^6$ lymphocytes of the first donor in the sense of a "mixed lymphocyte culture" and when $1 \times 10^7$ to $5 \times 10^7$ indicator particles according to the invention are added to this mixture, the degree of incompatibility of the two lymphocyte populations can be determined because of the changed migration speed of the particles in the electric field. The test result has led to a conclusion of the degree of relationship of the donors in the broader sense. Important fields of application are genetic studies and investigations on transplantations of organs.

In contradistinction to the conventional mixed lymphocyte culture, which provides a result after 5 to 6 days, the electrophoretic system using indicator particles allows the result to be obtained already after about two hours.

The following Examples illustrated the invention.

EXAMPLE 1

23 Milliliters of venous blood are taken from a test person by means of a syringe containing 0.5 ml of heparin. The blood sample was fed into a column (diameter 2 cm, height 30 cm), which was filled with glass beads (2 mm in diameter), and allowed to stand in an incubator for 90 minutes at 37° C. The eluate obtained from the column was then diluted in a ratio of 1:4 with Hank's solution containing 0.05% of $Na_2$-salt of ethylene-diamine tetracetic acid (EDTA). The dilute eluate was floated as a layer on one fourth its volume of a solution consisting of the sodium, calcium, magnesium and methyl-glucamine salts of metrizoic acid (RONPACON®, manufactured by Cilag-Chemie GmbH, Alsbach, W. Germany) and a high-molecular-weight copolymer of saccharose and epichlorhydrin (FICOLL® manufactured by Pharmacia, Uppsala, Sweden) and having a density of 1.074, and centrifuged for 15 minutes at 250G. The ring of lymphocytes lying above the density gradient was siphoned off and washed once with Hank's solution + EDTA, then twice with Hank's solution. The cells were centrifuged off and taken up in 0.5 ml of Dulbecco's medium without serum.

Dulbecco's medium is a culture medium used for cell growth and consisting of a mixture of amino acids, vitamins, inorganic salts, buffer substances and antibiotics. It is commercially available.

The number of cells was determined in a Coulter counter (manufactured by Coulter Electronics, Krefeld, W. Germany), and the lymphocyte suspension was standardized to $1 \times 10^7$ cells by means of Dulbecco's medium. Per 0.7 ml of this cell suspension, 3 ml of the solution of the encephalitogenic factor (EF) (0.3 mg EF per 1 ml of Hank's) were added, and the mixture was incubated for 24 hours. The lymphocytes were then separated by centrifuging, and 3 ml of the supernatant were incubated for 1 to 2 hours with 1 ml of a cell suspension ($5 \times 10^7$ stable and tanned erythrocytes per ml of Hank's). This cell suspension was the filled into a cytopherometer for measuring, and the electrophoretic migration of the particles was evaluated diagnostically for the presence of a cancerous disease. A cytopherometer is a microscope which is suitable for determining the electric surface charge of suspended microscopic particles from their migration speed in an electric field (electrophoresis). The suspension used therefor is contained in a measuring chamber of a so-called electrophoresis system. The optical axis of the microscope is arranged in a horizontal position since the measuring chamber has to be a vertical position in order to exclude any influences liable to falsify the measurements of the migration speed.

EXAMPLE 2

When, instead of EF as in Example 1, 3 ml of a solution of purified tuberculin (150,000 U/ml) were used, the measuring of the electrophoretic migration of the particles permitted the diagnosis of a sensitization of the test person to tuberculo-protein.

EXAMPLE 3

When instead of EF as in Example 1, 3 ml of a solution of tetanus toxoid (20 Lf/ml) were used, the measuring of the electrophoretic migration of the particles permitted the diagnosis of a sensitization of the test person to toxoid or toxin.

EXAMPLE 4

20 Milliliters of heparinized venous blood of a test person were diluted with 1:2 Hank's solution, and the dilution was floated on a two-layer gradient consisting each of 30 ml of a solution of different density, an upper layer A consisting of sodium, calcium, magnesium and methyl glucamine salts of metrizoic acid (Ronpacon ® manufactured by Cilag-Chemie GmbH, Alsbach) and of a high-molecular-weight copolymer of saccharose and epichlorhydrin (Ficoll ®, manufactured by Pharmacia, Uppsala) having a density of 1.077, and a lower layer B consisting of the same substances but having a density of 1.119. Applied on the gradient, the dilution was centrifuged for 20 minutes at 800 G. The lymphocyte ring atop layer A was siphoned off, washed three times with Hank's solution, and the lymphocytes thus obtained were taken up in Dulbecco's medium. The shaped blood constituents liable to interfere with the measuring, especially granulocytes and erythrocytes, were held in the boundary layer between layers A and B, or settled at the bottom of the gradient vessel.

The test mixture was prepared from $1 \times 10^6$ lymphocytes and $5 \times 10^7$ indicator particles (tanned erythrocytes treated with sulfosalicyclic acid according to the invention) while adding the antigen EF in a concentration of 0.3 mg/ml in a total volume of 3.5 ml. After having been incubated for 60 minutes, the mixture was fed to a cytopherometer, and the electrophoretic migration of the indicator particles contained in the mixture was determined. A slowed-down migration speed of the indicator particles was evidence of the presence of a malign disease in the test person. A corresponding test mixture having no antigen served as a control.

EXAMPLE 5

When as in Example 4 a test mixture was prepared from lymphocytes of a test peron, instead of a soluble antigen EF, and from $1 \times 10^6$ lymphocytes of a second not related test person and incubated as a mixed lymphocyte culture, and when to this mixture, as in Example 4, $5 \times 10^7$ indicator particles were added, it was possible after measuring the migration speed of the indicator particles in a cytopherometer to determine the degree of incompatibility between the two lymphocyte populations or the test persons, for example in the sense of a donor-donee selection for a transplantation of organs.

We claim:

1. In an in vitro diagnostic method wherein lymphocytes are incubated with antigens, the incubation mixture or the cell-free supernatant thereof is added to a dispersion of macrophages, and the migration speed of the macrophages is measured in an electric field, the improvement wherein said incubation mixture or cell-free supernatant is added to a dispersion of particles other than macrophages, said particles being interactive with said incubation mixture or supernatant whereby their behavior in the electric field is modified in a detectable manner, and said particles further showing a substantially uniform behavior in the electric field.

2. A method as in claim 1 wherein said particles are denatured erythrocytes.

3. A method as in claim 2 wherein said denatured erythrocytes are tanned erythrocytes stabilized with sulfosalicylic acid.

4. A method as in claim 1 wherein said particles are latex particles.

* * * * *